(12) United States Patent
Juergens

(10) Patent No.: US 11,857,165 B2
(45) Date of Patent: Jan. 2, 2024

(54) METHOD FOR ENDOSCOPIC IMAGING, ENDOSCOPIC IMAGING SYSTEM AND SOFTWARE PROGRAM PRODUCT

(71) Applicant: OLYMPUS WINTER & IBE GMBH, Hamburg (DE)

(72) Inventor: Thorsten Juergens, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 306 days.

(21) Appl. No.: 17/351,475

(22) Filed: Jun. 18, 2021

(65) Prior Publication Data
US 2021/0397865 A1 Dec. 23, 2021

(30) Foreign Application Priority Data
Jun. 23, 2020 (DE) .......................... 102020116473.4

(51) Int. Cl.
*G06T 7/00* (2017.01)
*A61B 1/04* (2006.01)
(Continued)

(52) U.S. Cl.
CPC ........ *A61B 1/043* (2013.01); *A61B 1/000094* (2022.02); *A61B 1/044* (2022.02);
(Continued)

(58) Field of Classification Search
CPC ......... A61B 1/05; A61B 1/051; A61B 1/0676; A61B 1/043; A61B 1/000094;
(Continued)

(56) References Cited

U.S. PATENT DOCUMENTS 9,775,497 B2 10/2017 Igarashi et al.
10,034,600 B2 7/2018 Igarashi
(Continued)

FOREIGN PATENT DOCUMENTS

DE 102011123037 B3 10/2019
JP 2005-027120 A 1/2005
(Continued)

*Primary Examiner* — Howard D Brown, Jr.
(74) *Attorney, Agent, or Firm* — Scully, Scott, Murphy & Presser, P.C.

(57) ABSTRACT

A method for endoscopic imaging including: capturing white light images with a video endoscope under white light illumination; evaluating the captured white light images for a structure having a predefined characteristic, when the presence of the structure having the predefined characteristic is found in a white light image, setting a special light imaging mode in which a light source generates special light illumination using the at least one special light and one or more images of a video stream are captured under the special light illumination and subjected to image processing in the set special light processing mode; identifying a subregion of the at least one white light image that contains the structure with the predefined characteristic and reading out only the subregion of a CMOS image sensor associated with the video endoscope, and processing the image data read out from the subregion as one or more special light images.

16 Claims, 2 Drawing Sheets

(51) Int. Cl.
  *G06V 10/141* (2022.01)
  *G06V 10/143* (2022.01)
  *A61B 1/06* (2006.01)
  *G06N 3/08* (2023.01)
  *H04N 5/265* (2006.01)
  *A61B 1/00* (2006.01)
  *G06F 18/214* (2023.01)
  *H04N 23/74* (2023.01)

(52) U.S. Cl.
  CPC .......... *A61B 1/0638* (2013.01); *A61B 1/0655* (2022.02); *G06F 18/214* (2023.01); *G06N 3/08* (2013.01); *G06V 10/141* (2022.01); *G06V 10/143* (2022.01); *H04N 5/265* (2013.01); *H04N 23/74* (2023.01); *G06V 2201/032* (2022.01)

(58) Field of Classification Search
  CPC ..... A61B 1/044; A61B 1/0638; A61B 1/0655; A61B 1/00006; A61B 1/045; A61B 1/063; A61B 1/04; A61B 1/00004; A61B 1/00009; A61B 1/00163; A61B 1/00186; G06F 18/214; G06N 3/08; G06V 10/141; G06V 10/143; G06V 2201/032; H04N 5/265; H04N 23/74
  See application file for complete search history.

(56) References Cited

U.S. PATENT DOCUMENTS

| | | |
|---|---|---|
| 2011/0295062 A1 | 12/2011 | Gratacós Solsona et al. |
| 2012/0327205 A1* | 12/2012 | Takahashi .......... G02B 23/2476 348/65 |
| 2016/0120398 A1 | 5/2016 | Kubo |
| 2020/0135330 A1* | 4/2020 | Sugie .................. G06V 10/147 |
| 2020/0138265 A1 | 5/2020 | Endo |

FOREIGN PATENT DOCUMENTS

| | | |
|---|---|---|
| JP | 2014-124331 A | 7/2014 |
| WO | 2019/239942 A1 | 12/2019 |

\* cited by examiner

METHOD FOR ENDOSCOPIC IMAGING, ENDOSCOPIC IMAGING SYSTEM AND SOFTWARE PROGRAM PRODUCT

CROSS-REFERENCE TO RELATED APPLICATION

The present application is based upon and claims the benefit to DE 10 2020 116 473.4 filed on Jun. 23, 2020, the entire contents of which are incorporated herein by reference.

BACKGROUND

Field

The present disclosure relates to a method for endoscopic imaging, to an endoscopic imaging system and to a software program product.

Prior Art

Modern endoscopic imaging systems offer a variety of special light imaging modes in addition to the white light mode with white light illumination, which comprises the entire RGB spectrum and is crucial for the visual spectrum (VIS). Such special light imaging (SLI) modes include, for example, narrow band imaging (NBI), near-infrared fluorescence imaging (NIRF) and red dichromatic imaging (RDI). RDI is a proprietary method of Olympus Corporation, which is described in the U.S. Pat. No. 10,034,600 B2 and U.S. Pat. No. 9,775,497 B2. This list is not exhaustive.

Near-infrared fluorescence imaging (NIRF) can be used to analyze and assess blood vessel perfusion, to confirm the anatomy of the hepatobiliary system, to find lymph nodes or to visualize the ureter following administration of an extrinsic contrast agent such as ICG (indocyanine green), CY5.5, ZW800 or ZW-1. Red dichromatic imaging (RDI) can be used to identify the source of arterial bleeding. Narrow band imaging (NBI) can help to differentiate between a benign hyperplasia and cancerous tissues or cancer precursors, for example between intestinal polyps of types NICE-1 and NICE-2, in order to decide whether or not a polyp needs to be resected.

Typical examinations and operations are carried out by a doctor using white light illumination for visual imaging (VIS). If the doctor discovers an abnormality in the white light images that requires closer examination in a special light imaging mode, the doctor selects the appropriate special light imaging mode based on their training and experience.

SUMMARY

Against this backdrop, an object is to assist the doctor during the examination or operation with an improved form of endoscopic imaging.

Such object can be achieved by a method for endoscopic imaging with an endoscopic imaging system which comprises a video endoscope having at least one CMOS image sensor, a light source unit configured to generate white light and at least one special light, an image evaluation unit, a control unit and a display device, wherein white light images are captured by the video endoscope under white light illumination and evaluated by the image evaluation unit in real time to check for the presence of at least one structure having at least one predefined characteristic, wherein, when the image evaluation unit detects the presence of at least one structure having at least one predefined characteristic in at least one white light image, a special light imaging mode is set in which the light source unit generates special light illumination using the at least one special light and one or more images of a video stream is or are captured under the special light illumination and is or are subjected to image processing in a special light processing mode that comprises identifying a subregion of the white light image that contains the structure with the predefined characteristic detected in the white light image and reading out only this subregion of the image sensor, wherein the image data read out from the subregion are further processed as a special light image or special light images.

Such method considers the fact that the majority of endoscopic video systems, i.e., video endoscopes or camera heads for endoscopes, are equipped with a CMOS image sensor instead of CCD image sensors. Unlike CCD image sensors, many CMOS image sensors can only be read out in subregions, so-called "regions of interest" (ROI), which significantly increases the reading rate. The subregion is typically a rectangular region that, within the context of this disclosure, is dimensioned such that it fully contains the structure, if applicable with a border that occupies, for example, 2% to 20% of the extent of the longer side of the rectangle. For example, an intestinal polyp typically occupies approximately 10% to 20% of the image area in the image. In many clinical situations, an ROI of this kind extends over an equivalent area in the full image. In such a case, a CMOS image sensor, which for example has a HD resolution of 1980×1080 pixels, can be read out exclusively and very quickly in a corresponding subregion that contains the polyp, for example in a rectangular region of which opposing corner points have the coordinates 600/200 and 1061/662, for example. The resulting ROI encompassing the intestinal polyp would then have a size of 461×462 pixels (approx. 213,000 pixels) and would therefore only be approximately one tenth of the size of the full HD image.

In such method, it is therefore possible to obtain a high image refresh rate even when a special light imaging mode has been activated, because the subregions of the CMOS image sensor are read out and processed more quickly than the entire image data of the CMOS image sensor are read out in the white light imaging mode. Without subregions being selected, the image refresh rate in the case of an alternating sequence of white light images and special light images would be halved, for example from 50 Hz to 25 Hz, wherein the white light image sequence would be at 25 Hz and the special light image sequence would also be at 25 Hz. In the event of rapid movements, this could lead to motion artifacts.

Many special light imaging modes are also faint. The required high light sensitivity or gain factors lead to significant image noise. The noise can be reduced by increasing the exposure time or by combining successive frames. These measures are severely restricted in normal time-sequential imaging without selection of subregions, whereas the higher image refresh rate possible according to the invention under special light conditions can be used to increase the effective exposure time of the special light images via their closer succession.

Such method also makes it possible to assist the treating physician by carrying out image recognition on the white light images in which structures with the predefined characteristic are automatically detected. Such structures may for example be perfused blood vessels, lymph nodes, arterial bleeding or intestinal polyps, however this list is not exhaustive. The predefined characteristics of these structures are well-known and well documented based on extensive image material and can be identified by means of automated image evaluation. In this case, suitable special light imaging by means of which the identified structure is shown in more detail and more precisely is set. The doctor is relieved of the decision to set the special light imaging mode, and they are shown the special light imaging without having to do anything.

An ongoing examination is usually processed as a video stream. Such method can be applied to the ongoing video stream, but also, if desired by the doctor, to individual images isolated from the video stream by means of a snapshot function to be used for closer examination and documentation.

The subregion can be selected in the image evaluation unit, and the instruction as to which subregion of the CMOS image sensor is read out can be issued either by the image evaluation unit directly or via the control unit. The image evaluation unit may also be integrated as software in the control unit as a functional unit, for example as a program or sub-routine of a program.

The normal situation in various examinations is that no relevant structures can be seen. In these cases, the white light images are advantageously displayed by means of the display device if the image evaluation unit detects no structure having at least one predefined characteristic in the white light images.

In embodiments, the special light image or special light images can be displayed alone or as a composite image or as composite images superimposed on white light images by means of the display device. Displaying the special light image alone has the advantage of being an undisturbed representation that can be easily interpreted by the trained eye of the doctor. Displaying a composite image, in which the special light image is congruently superimposed on the white light image at the location of the structure, offers the advantage of embedding the special light image in the surrounding structures. A fused image or composite image of this kind can be referred to as an augmented reality image (ARI). For the composite image, the special light image can be superimposed on the white light image with a certain degree of transparency, for example between 5% and 50%, such that the underlying structures of the white light image that are not visible in the special light image can still be seen, or non-transparently with a degree of transparency of 0% to 5%.

In embodiments with a composite image sequence displayed in a video stream, in cases where the image evaluation unit detects the presence of at least one structure having at least one predefined characteristic in the white light images, alternating white light and special light illumination can be generated synchronized with the video image sequence, wherein in each case one pair consisting of a white light image and a special light image is processed and combined into a composite image. Individual frames from this composite image video stream can be captured using the snapshot function and used for closer examination and for documentation. Therefore, within the scope of this disclosure, the term "special light imaging mode" also includes cases where white light images and special light images are captured in an alternating sequence, processed further and put together.

In one embodiment, the video image sequence and the synchronized alternating white light and special light illumination can occur in a temporal rhythm in which the duration of the special light illumination and special light image capture is shorter than the duration of the white light illumination and white light image capture. This is possible because only one subregion of the CMOS image sensor is read out in each case for the special light image captures and only the image data of said subregion are processed further in the image evaluation unit, especially since no structure recognition is applied to the special light images. Therefore, it is no longer necessary to halve the frequency of the image display, i.e., the succession of the individual frames, but rather it is possible to achieve an image sequence with a similarly high frequency to the purely white light video sequence, as a result of which motion artifacts are largely prevented. One possibility for implementing this consists in the control unit, which may be integrated with the image evaluation unit, instructing the image sensor in the video endoscope and the light source unit to capture images or subimages in a correspondingly synchronized temporal sequence and to provide white light illumination and special light illumination.

In embodiments, the light source unit can be configured to generate one or more of the following as special light: illumination for narrow band imaging (NBI), alumination for near-infrared fluorescence imaging (NIRF) and illumination for red dichromatic imaging (RDI), wherein RDI illumination is generated in the case of detected bleeding and/or NBI illumination is generated in the case of detected intestinal polyps. The image evaluation device may be configured to select one of multiple special light modes available based on the detected structure having the predefined characteristic. Alternatively, the predefined characteristic and the special light mode may be preselected and set. This may be useful, for example, in the case of examinations which search for specific structures, for example in colonoscopies or operations in which bleeding are to be expected, detected and stopped.

In embodiments, the structure having at least one predefined characteristic can be detected and/or the subregion containing the structure can be selected and/or the special light mode can be selected by means of an image evaluation algorithm based on artificial intelligence. The image evaluation algorithm may, in such cases, be based on one or more classifying neural networks, such as, CNN, which has or have been pretrained using white light images containing structures having at least one predefined characteristic.

In an extension, in embodiments, the image evaluation unit can evaluate the special light images to check for the presence of a corresponding structure, for example, confirms the existence of the structure or otherwise prompts departure from the special light imaging mode again. The special light imaging modes can be used for showing the relevant structures in a very high-contrast and thus clearly recognizable manner, such that evaluation of the special light images with regard to these structures yields a high significance with regard to the presence of corresponding structures. Corresponding image evaluation is also quicker than in the white light images, because only one subregion of the white light image is present in the special light image and thus a smaller amount of data has to be evaluated.

Such object can also be achieved by an endoscopic imaging system, comprising a video endoscope having at least one CMOS image sensor, a light source unit configured to generate white light and at least one special light, an image evaluation unit, a control unit and a display device, wherein the control unit is connected to the light source unit, video endoscope and image evaluation unit for signaling and the image evaluation unit is connected to the video endoscope for signaling, wherein the imaging system having the video endoscope, light source unit, image evaluation unit, control unit and display device is configured to carry out an above-described method.

The video endoscope of the imaging system may comprise a CMOS sensor either in the distal region of the endoscope shaft or in the handle or be configured as a combination of an endoscope with a camera head that comprises a CMOS sensor as an image sensor.

Furthermore, such object can also be achieved by a software program product comprising program code for an endoscopic imaging system, comprising an image evaluation program component that is executed in the image evaluation unit of the imaging system, and a control program component that is executed in the control unit of the imaging system, wherein the image evaluation program component and the control program component are configured to carry out an above-described method when they are executed in the image evaluation unit and control unit.

The endoscopic imaging system and the software program product can relate to the above-described method and can realize its advantages, features and properties in the same way.

Further features will become apparent from the description of embodiments together with the claims and the attached drawings. Embodiments can fulfill individual features or a combination of several features.

BRIEF DESCRIPTION OF THE DRAWINGS

The embodiments are described below, without restricting the general idea of the invention, based on the exemplary embodiments in reference to the drawings, whereby we expressly refer to the drawings with regard to all details that are not explained in greater detail in the text. In the figures.

DETAILED DESCRIPTION

Figure 1:
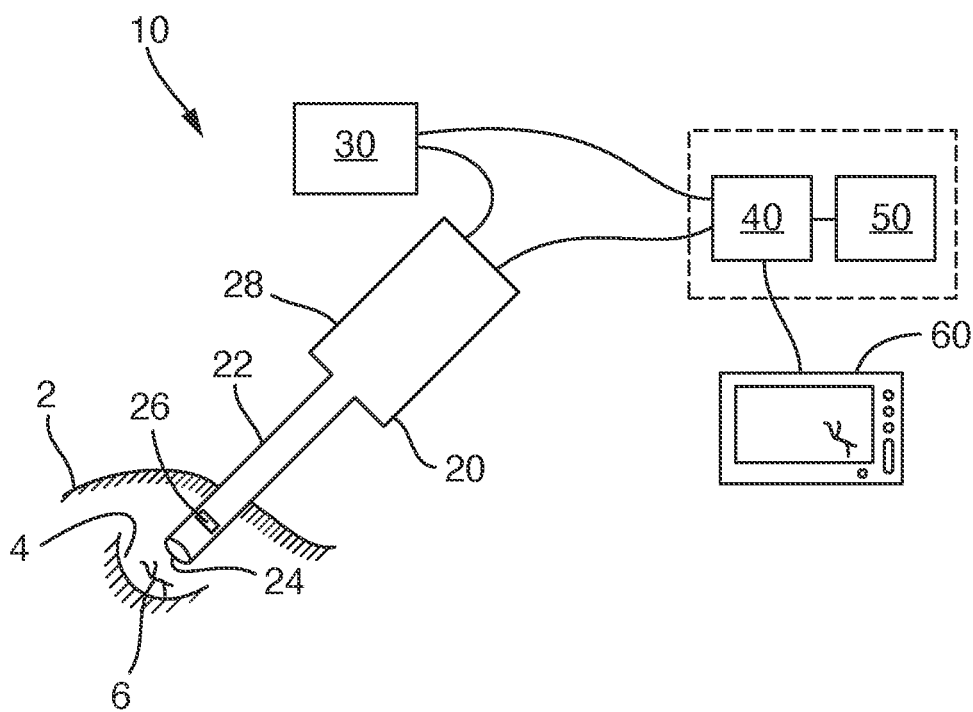
FIG. 1 illustrates is a schematic representation of an endoscopic imaging system.

In the drawings, the same or similar elements and/or parts are provided with the same reference numbers in each case; a reintroduction will therefore always be omitted.

FIG. 1 is a schematic representation of an endoscopic imaging system 10 in an operation situation. An examination in which a structure 6 having a predefined characteristic is discovered, for example an intestinal polyp, bleeding, a perfused blood vessel, etc., is carried out by means of a video endoscope 20 in a body cavity 4 of a body 2 of a patient.

The video endoscope 20 comprises an endoscope shaft 22 on a handle 28, on the distal end of which shaft 22 a CMOS image sensor 26 is arranged behind an entry lens 24 and an optical system not shown here. Alternatively, the video endoscope 20 may also be configured as a combination of a conventional endoscope with a camera head having the CMOS sensor attached to a proximal portion of the handle 28.

The video endoscope 20 is connected to a light source unit 30, which may also be part of the video endoscope 20 or, alternatively, part of a control device of the endoscopic imaging system 10. The light source unit 30, having various light sources and filter units, is configured to generate white light and special light alternately according to one or more special light illumination procedures, which light is directed through the video endoscope 20 into the body cavity 4 and illuminates the examination surroundings.

The imaging system 10 further comprises an image evaluation unit 40 and a control unit 50, which are also connected to the light source unit 30 and to the video endoscope 20, as well as a display device 60, which is connected to the image evaluation unit 40. The various components, such as, the image evaluation unit 40 and the control unit 50, are configured to carry out the method for endoscopic imaging. For this purpose, they are equipped with program code that perform the image evaluation and control. The evaluation unit 40 and control unit 50, although shown separately in the Figures, may be configured from a single controller.

Figure 2:
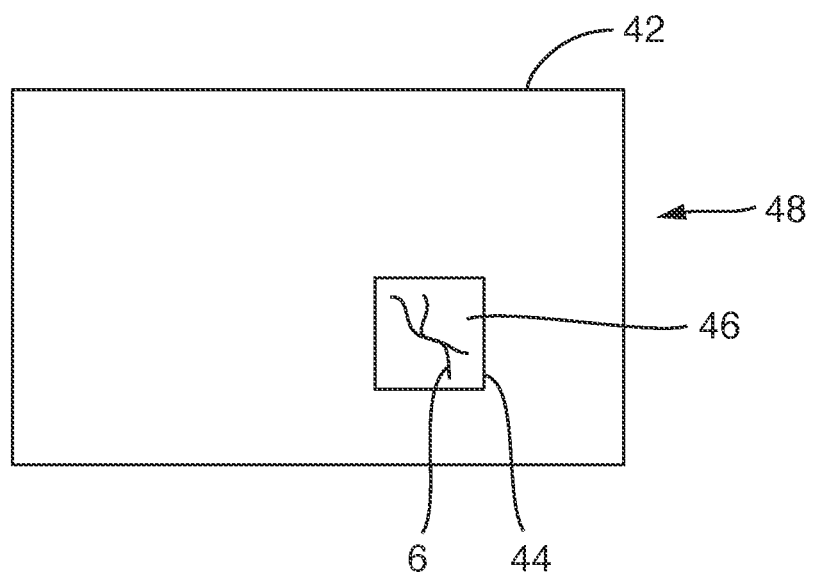
FIG. 2 illustrates a schematic representation of the imaging concept.

FIG. 2 shows the imaging concept in schematic form. The imaging and image acquisition are based on the capture of white light images 42 that are subjected to evaluation by means of the image evaluation unit 40. A white light image 42 of this kind may for example have a HD resolution and is generated from the light source unit 30 under white light illumination. If the white light image 42 comprises a structure 6 having a predefined characteristic, for example the characteristic of a perfused vessel, bleeding, an intestinal polyp, etc., the image evaluation unit 40 identifies the subregion 44 of the white light image 42 that contains the structure 6.

Because a structure 6 was detected, special light illumination for special light imaging is set for the following image and the CMOS sensor 26 is read out only in the subregion 44. A representation, such as, false-color representation, of the read-out subregion 44 is superimposed at the correct position on the white light image 42 as a special light image 46, producing a composite image 48 that is displayed to the treating physician on the display device 60. The composite image 48 may be part of a video stream in the special light imaging mode, in which in each case pairs of white light images and special light images are captured and combined or used as an individual image for closer examination and for documentation. In the case of a video stream in the special light imaging mode, each white light image can be analyzed and the subregion 44 can be redetermined, since the video endoscope 20 and the structure 6 can move relative to one another.

The selection of the specific special light imaging mode can be done either a priori by the doctor, who is for example carrying out a specific examination, for example a colonoscopy, in which only one special light imaging mode is relevant, or an image evaluation algorithm in the image evaluation unit 40 can decide which special light imaging mode is selected based on the structure 6 found. A selection algorithm of this kind may for example be based on neural networks that have been trained using previously captured white light images having the corresponding structures in order to identify and classify the corresponding structures and the respectively optimal special light imaging modes.

Figure 3:
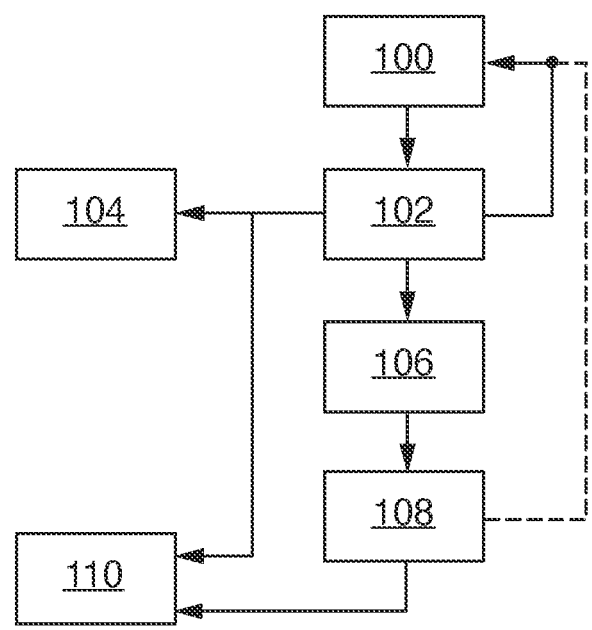
FIG. 3 illustrates an exemplary flow diagram for a method for endoscopic imaging.

FIG. 3 is an exemplary flow diagram for a method for endoscopic imaging It begins with the capture of a white light image 42 (method step 100), which is then analyzed to check for the presence of a structure 6 having a predefined characteristic (method step 102). If no structure 6 is found, the white light image 42 is displayed as such (method step 104) and a new white light image 42 is captured (method step 100). If a structure 6 is in fact found in the white light image 42, the subregion 44 in which the structure 6 is located in the white light image 42 is identified. Subsequently, a preset or suitable special light imaging mode with corresponding special light illumination is set (method step 106), an image is captured under the special light illumination that has been set and the image data of the CMOS image sensor 26 are read out only in the subregion 44 and further processed as a special light image 46 (method step 108). The special light image 46 is then superimposed on the white light image 42 and displayed as a composite image 48 (method step 110). The process is repeated from method step 100 until the examination is complete or until the examination mode is terminated.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims

LIST OF REFERENCE NUMBERS

2 Body
4 Body cavity
6 Structure
10 Endoscopic imaging system
20 Video endoscope
22 Endoscope shaft
24 Entry lens
26 CMOS image sensor
28 Handle
30 Light source unit
40 Image evaluation unit
42 White light image
44 Subregion
46 Special light image
48 Composite image
50 Control unit
60 Display device
100 Capture of the white light image
102 Analysis of the white light image
104 Display of the white light image
106 Setting of a special light imaging mode
108 Capture of a special light image
110 Generation and display of a composite image

What is claimed is:

1. A method for endoscopic imaging with an endoscopic imaging system, the endoscopic imaging system comprising a video endoscope having at least one CMOS image sensor, a light source configured to generate white light and at least one special light, and a controller, the method comprising:
   capturing white light images with the video endoscope under white light illumination in a white light imaging mode;
   evaluating the white light images captured in the white light imaging mode in real time by the controller to detect whether at least one structure having at least one predefined characteristic is present in the white light images captured in the white light imaging mode,
   when the presence of the at least one structure having the at least one predefined characteristic is detected in at least one white light image of the evaluated white light images, switching from the white light imaging mode to a special light imaging mode in which the light source generates special light illumination other than white light imaging using the at least one special light and one or more images of a video stream are captured under the special light illumination and subjected to image processing in the special light processing mode;
   identifying a subregion of the at least one white light image that contains the detected at least one structure with the predefined characteristic and reading out only a corresponding subregion of the image sensor, and
   processing the image data read out from the corresponding subregion as one or more special light images.

2. The method according to claim 1, wherein the white light images are displayed on a display if the controller detects no structure having the at least one predefined characteristic in the white light images.

3. The method according to claim 1, wherein the one or more special light images are displayed alone, as a composite image or as composite images superimposed on white light images on a display.

4. The method according to claim 1, further comprising, where the controller detects the presence of the at least one structure having the at least one predefined characteristic in the white light images, generating alternating white light and special light illumination synchronized with the video image sequence, wherein one pair consisting of a white light image and a special light image is processed and combined into a composite image.

5. The method according to claim 4, wherein the video image sequence and the synchronized alternating white light and special light illumination occurs in a temporal rhythm in which the duration of the special light illumination and special light image capture is shorter than the duration of the white light illumination and white light image capture.

6. The method according to claim 1, wherein the light source is configured to generate one or more of the following as special light: illumination for narrow band imaging (NBI), illumination for near-infrared fluorescence imaging (NIRF) and illumination for red dichromatic imaging (RDI).

7. The method according to claim 6, wherein the RDI illumination is generated in the case of detected bleeding.

8. The method according to claim 6, wherein the NBI illumination is generated in the case of detected intestinal polyps.

9. The method according to claim 1, wherein the controller is configured to select one of multiple special light modes available based on the detected structure having the predefined characteristic.

10. The method according to claim 1, wherein the predefined characteristic and the special light mode are preselected.

11. The method according to claim 1, wherein one or more of the structure having the at least one predefined characteristic is detected, the subregion containing the structure, and the special light mode is selected by an image evaluation algorithm based on artificial intelligence.

12. The method according to claim 11, wherein the image evaluation algorithm is based on one or more classifying neural networks.

13. The method according to claim 12, wherein the one or more classifying neural networks has been pretrained using white light images containing the structures having the at least one predefined characteristic.

14. The method according to claim 1, wherein the controller evaluates the special light images to check for the presence of a corresponding structure.

15. An endoscopic imaging system comprising:
   a video endoscope having at least one CMOS image sensor;
   a light source configured to generate white light and at least one special light other than the white light; and a controller connected to the light source and to the at least one CMOS image sensor, the controller being configured to:

capture white light images with the video endoscope under white light illumination in a white light imaging mode;

evaluate the white light images captured in the white light imaging mode in real time to detect whether at least one structure having at least one predefined characteristic is present in the white light images captured in the white light imaging mode, when the presence of the at least one structure having the at least one predefined characteristic is detected in at least one white light image, of the evaluated white light images, switch from the white light imaging mode to a special light imaging mode in which the light source generates special light illumination other than white light imaging using the at least one special light and one or more images of a video stream are captured under the special light illumination and subjected to image processing in the special light processing mode;

identify a subregion of the at least one white light image that contains the detected at least one structure with the predefined characteristic and reading out only a corresponding subregion of the image sensor, and processing the image data read out from the corresponding subregion as one or more special light images.

16. Non-transitory computer-readable storage medium storing instructions that cause a computer to at least perform a method for endoscopic imaging with an endoscopic imaging system, the endoscopic imaging system comprising a video endoscope having at least one CMOS image sensor, a light source configured to generate white light and at least one special light, and a controller, the method comprising:

capturing white light images with the video endoscope under white light illumination in a white light imaging mode;

evaluating the white light images captured in the white light imaging mode in real time by the controller to detect whether at least one structure having at least one predefined characteristic is present in the white light images captured in the white light imaging mode, when the presence of the at least one structure having the at least one predefined characteristic is detected in at least one white light image of the evaluated white light images, switching from the white light imaging mode to a special light imaging mode in which the light source generates special light illumination other than white light imaging using the at least one special light and one or more images of a video stream are captured under the special light illumination and subjected to image processing in the special light processing mode;

identifying a subregion of the at least one white light image that contains the detected at least one structure with the predefined characteristic and reading out only a corresponding subregion of the image sensor, and processing the image data read out from the corresponding subregion as one or more special light images.

* * * * *